US010513633B2

(12) United States Patent
Doucette et al.

(10) Patent No.: US 10,513,633 B2
(45) Date of Patent: Dec. 24, 2019

(54) FLOOR COATING COMPOSITIONS AND RELATED METHODS

(71) Applicant: Red Alert Wax, LLC, Louisville, KY (US)

(72) Inventors: Robert L. Doucette, Louisville, KY (US); Michael Ursini, Louisville, KY (US); Michael Jackson, Louisville, KY (US)

(73) Assignee: RED ALERT WAX, LLC, Louisville, KY (US)

( * ) Notice: Subject to any disclaimer, the term of this patent is extended or adjusted under 35 U.S.C. 154(b) by 0 days.

(21) Appl. No.: 15/107,052

(22) PCT Filed: Jun. 10, 2016

(86) PCT No.: PCT/US2016/036841
§ 371 (c)(1),
(2) Date: Jun. 21, 2016

(87) PCT Pub. No.: WO2016/201191
PCT Pub. Date: Dec. 15, 2016

(65) Prior Publication Data
US 2018/0079932 A1 Mar. 22, 2018

Related U.S. Application Data

(60) Provisional application No. 62/174,180, filed on Jun. 11, 2015.

(51) Int. Cl.
C09G 1/04 (2006.01)
C09G 1/16 (2006.01)
C09D 7/00 (2018.01)
C09D 1/00 (2006.01)
C07C 39/04 (2006.01)
C09D 5/00 (2006.01)
C09D 7/20 (2018.01)
C09D 7/40 (2018.01)
C09D 7/41 (2018.01)
C07D 307/885 (2006.01)
C09D 133/08 (2006.01)

(52) U.S. Cl.
CPC .............. C09G 1/04 (2013.01); C07C 39/04 (2013.01); C07D 307/885 (2013.01); C09D 1/00 (2013.01); C09D 5/00 (2013.01); C09D 7/20 (2018.01); C09D 7/40 (2018.01); C09D 7/41 (2018.01); C09D 133/08 (2013.01); C09G 1/16 (2013.01)

(58) Field of Classification Search
CPC .......... C09D 7/12; C09D 1/00; C09D 133/08; C07D 307/885; C07D 7/00; C07D 1/00; C07C 39/04; C09G 1/04; C09G 1/16
USPC ........................................... 524/424
See application file for complete search history.

(56) References Cited

U.S. PATENT DOCUMENTS

| 3,855,170 | A | 12/1974 | Junkin et al. |
| 4,070,510 | A * | 1/1978 | Kahn ................... C09G 1/16 106/10 |
| 4,071,645 | A | 1/1978 | Kahn |
| 4,971,631 | A | 11/1990 | Sallee et al. |
| 5,110,492 | A | 5/1992 | Casey |
| 5,482,654 | A | 1/1996 | Luttrell et al. |
| 6,894,095 | B2 | 5/2005 | Russo et al. |
| 8,067,350 | B2 | 11/2011 | Wenzel et al. |
| 8,133,403 | B2 | 3/2012 | Li et al. |
| 2003/0220213 | A1 | 11/2003 | Bober |
| 2005/0166797 | A1 * | 8/2005 | Li ........................ C09G 1/00 106/203.1 |
| 2006/0293205 | A1 | 12/2006 | Chung |
| 2009/0208546 | A1 * | 8/2009 | Shirley ................ A01N 25/10 424/405 |
| 2012/0132103 | A1 | 5/2012 | Tsugita et al. |

FOREIGN PATENT DOCUMENTS

WO 2005071032 A2 8/2005

OTHER PUBLICATIONS

United States Patent and Trademark Office, International Search Report issued in corresponding Application No. PCT/US2016/036841 dated Aug. 30, 2016.

* cited by examiner

Primary Examiner — Deve V Hall
(74) Attorney, Agent, or Firm — Stites & Harbison, PLLC; Terry L. Wright; David W. Nagle, Jr.

(57) ABSTRACT

Floor coating compositions and methods of forming a floor coating composition are provided. The floor coating composition includes an acrylic wax, water, and an indicator that includes a color at a first pH and that is colorless at a second pH. The method of forming a floor coating includes milling distilled water and an indicator, slowly adding an acrylic wax, slowly adding a pre-mixed solution of distilled water and an alkaline material, and then mixing the ingredients to form the composition.

5 Claims, No Drawings

FLOOR COATING COMPOSITIONS AND RELATED METHODS

RELATED APPLICATIONS

This application claims priority from U.S. Provisional Application Ser. No. 62/174,180, filed Jun. 11, 2015, the entire disclosure of which is incorporated herein by this reference.

TECHNICAL FIELD

The presently-disclosed subject matter relates to floor coating compositions. In particular, the presently-disclosed subject matter relates to floor coating compositions comprising a visually disappearing indicator as well as methods for making and using the same.

BACKGROUND

In most industrial and commercial buildings, such as retail stores, hospitals, restaurants, health care homes, and schools, the floors are comprised of tile, vinyl, or concrete. These and other types of flooring materials can be coated with a finish, such as a wax or sealant, to protect the underlying floor. When applying such a finish to those floors, however, the floors are often waxed to a high gloss and become exceedingly smooth, such that only a small amount of water on the floors will cause the floors to become slick. Indeed, one of the most frequent accidents encountered in industrial and commercial buildings are "slip and fall" accidents that arise due to unseen "slick spots" on finished waxed floors.

In light of the frequency of slip and fall accidents, many companies have been forced to place barriers or large signs adjacent to a wet area of a floor in order to alert individuals of a possible slipping hazard. However, because one has to first become aware of a potential wet area, there is an inherent delay from time a spill occurs to when individuals are alerted of the wet area. Furthermore, since barriers and large signs are often left in place for extended periods of time, which frequently continue long after a previously wet floor has dried, the use of barriers and large signs may be ineffective as a number of individuals will simply ignore the safety barriers or signs and walk on the wet floor.

Accordingly, there remains a need in the art for a floor finish composition that can effectively and economically be applied over a desired area. There also remains a need for a floor finish composition that can quickly and effectively warn the public of wet floor conditions, thereby reducing the possibility of slip and fall accidents.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this Summary does not list or suggest all possible combinations of such features.

In some embodiments of the presently-disclosed subject matter, floor coating compositions and methods for making a floor coating composition are provided. In some embodiments, a floor coating composition includes an acrylic wax, water, and an indicator that includes a color at a first pH and that is colorless at a second pH. In some embodiments, the composition also includes an alkaline material. In some embodiments, for example, the alkaline material includes sodium carbonate. In some embodiments, the composition includes at least one of a pigment dispersant and an anti-foaming agent. In some embodiments, the composition provides a floor coating that changes color when a liquid, such as water, is positioned in contact therewith. Additionally or alternatively, the color of the composition may reverse or disappear upon removal of the liquid.

In some embodiments, the method for making a floor coating composition includes milling distilled water and an indicator, slowly adding an acrylic wax, slowly adding a pre-mixed solution of distilled water and an alkaline material, and then mixing the ingredients to form the composition. In some embodiments, the indicator includes phenolphthalein. In some embodiments, the alkaline material includes sodium carbonate. In some embodiments, the milling step further includes milling at least one of a pigment dispersant and an anti-foaming agent with the distilled water and the indicator. In some embodiments, the floor coating composition is arranged and disposed to include a color at a first pH and be colorless at a second pH.

Further features and advantages of the present invention will become evident to those of ordinary skill in the art after a study of the description, figures, and non-limiting examples in this document.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth herein to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter includes floor coating compositions and methods for indicating the presence of a liquid on a floor surface. In some embodiments the compositions can visually display a color at a first pH and can be colorless at a second pH. In some embodiments, the present compositions visually display a color when the composition is in a wet, uncured state, and can be colorless when the composition is cured.

In this respect, embodiments of the presently-disclosed composition solve many of the shortcomings of known floor finishes. Embodiments of the compositions can be applied when the composition visually displays a color, thereby identifying whether a surface has been coated with the composition. This can facilitate application of the composition on a surface, avoid repeated application of the composition on the same surface, and can help ensure that the composition is of a proper thickness and achieves full surface coverage.

In further embodiments, the composition in a cured state can visually display a color when it is exposed to a liquid, such as water. For instance, a colorless composition that has been applied to and has cured on a surface can visually display a color when exposed to water from a leaky faucet, spilt beverage, or the like. This visual indicator can supplement or take the place of physical warning stands and signs that often are placed around spills. In some embodiments, the composition will return to a colorless state once the liquid evaporates from the composition. Additionally or alternatively, in some embodiments, the composition is capable of continually and/or repeatedly displaying a color when exposed to water for an extended period of time. For example, the composition may continually and/or repeatedly display a color upon exposure to water for at least 10 days, at least 20 days, at least 30 days, at least 40 days, at least 50 days, at least 60 days, at least 70 days, at least 80 days, up to 6 months, up to 12 months, between 10 days and 12 months, between 10 days and 9 months, between 10 days and 6 months, between 10 days and 80 days, between 45 days and 80 days, between 60 days and 80 days, or any combination, sub-combination, range, or sub-range thereof.

Some embodiments of the presently-disclosed compositions comprise an acrylic wax, water, and an indicator that includes a color at a first pH and that is colorless at a second pH. As described above, the composition can transition from a colored state at a first pH to a colorless state at a second pH as the composition cures and/or as liquid evaporates from a surface of the composition. In some embodiments the first pH is higher than the second pH. For example, in some embodiments the first pH is greater than about pH 7.0, greater than about pH 8.0, greater than about pH 9.0, greater than about pH 10.0, greater than about pH 11.0, or greater than about pH 12.0. In some embodiments the first pH is about pH 7.5, about pH 8.0, about pH 8.5, about pH 9.0, about pH 9.5, about pH 10.0, about pH 10.5, about pH 11.0, about pH 11.5, or to about pH 12.0. In some embodiments the composition visually displays a color when at a pH equal to or greater than neutral pH.

The acrylic wax of the present compositions can include an acrylic polymer that includes acrylic monomers. In some embodiments the acrylic wax is an acrylic copolymer comprising acrylic monomers and one or more other types of monomers, and therefore the term "acrylic polymer" as used herein can be inclusive of "acrylic copolymers." In other embodiments, the acrylic wax includes a polymer emulsion that comprises the presently-disclosed acrylic polymers. Those of ordinary skill in the art will recognize that the terms "vehicle," "polymer," "polymer emulsion," "wax concentrate," and the like can be used interchangeably herein to refer to an acrylic wax.

The term "acrylic" as used herein refers to monomers of acrylic acid or acrylate. Exemplary acrylic monomers include lower alkyl esters of acrylic acid, methacrylic acid, or mixtures thereof. For example, acrylic monomers may include methyl methacrylate, ethyl acrylate, butyl acrylate, methacrylic acid, and combinations thereof.

The term "alkyl" refers to alkyl groups with the general formula $C_nH_{2n+1}$, where n=about 1 to about 18 or more. The groups can be straight-chained or branched. Alkyl, when used herein, can also comprise "lower alkyls," which refer to alkyl groups with the general formula $C_nH_{2n+1}$, where n=1 to about 6. In some embodiments, n=1 to about 3. Examples include methyl, ethyl, propyl, isopropyl, n-butyl, sec-butyl, t-butyl, isobutyl, n-pentyl, isopentyl, neopentyl, n-hexyl, and the like.

The concentration of acrylic monomers in an acrylic wax can be varied to adjust the viscosity, UV durability, hardness, application properties, or the like of the composition. Some acrylic waxes can comprise about 25 wt %, about 50 wt %, about 75 wt %, or about 100 wt % of acrylic monomers. For example, some acrylic waxes comprise copolymers that include about 25 wt %, about 50 wt %, about 75 wt %, or about 100 wt % of acrylic monomers. As a further example, in some embodiments the acrylic wax is a polymer emulsion that comprises about 25 wt %, about 50 wt %, about 75 wt %, or about 100 wt % of acrylic monomers and/or acrylic polymers. For acrylic waxes that do not comprises 100 wt % of acrylic monomers, the portion of the acrylic waxes that do not comprise the acrylic monomers can comprise one or more other types of monomers and/or polymers. For example, some embodiments of compositions comprise an acrylic wax that includes styrene monomers. As such, exemplary acrylic waxes can include an acrylic-styrene copolymer and/or an emulsion of acrylic polymers and styrene polymers.

In some embodiments, the present compositions further include a coalescing agent. In some instances coalescing agents can catalyze and/or permit curing of the composition within a particular temperature range, such as a temperature from about 40° F. to about 120° F. In some embodiments the coalescing agent includes a glycol ether. In specific embodiments the coalescing agent is selected from 2-(2-ethoxyethoxy)ethanol, diethylene glycol monohexylether, diethylene glycol 2-ethyl hexyl ether, ethylene glycol monobutylether, 2-ethyl hexanol, isooctylalcohol, and combinations thereof.

In some embodiments, the present compositions further include a plasticizer. In some instances a plasticizer can soften a composition or make it more pliable. Thus, some plasticizers can soften the composition to make it less brittle, more workable, and/or otherwise improve the handling properties of composition. The plasticizer may evaporate or otherwise diffuse out of the composition over time. Exemplary plasticizers include, but are not limited to, phthalate esters such as butylbenzyl phthalate, dibutyl phthalate, 2-ethylhexylbenzyl phthalate, dicyclohexyl phthalate, dibenzyl phthalate, butylcyclohexyl phthalate, di-2-ethylhexyl ester of hexamethylene diphthalate, and di-(methylcyclohexyl) phthalate. Still further plasticizers can include mixed benzoic acid and fatty oil acid esters of pentaerythritol, poly(propylene adipate) dibenzoate, diethylene glycol dibenzoate, ethylene glycol adipate benzoate, and/or neopentyl glycol adipate benzoate. Other exemplary plasticizers include tetrabutylthiodisuccinate, butylphthalyl butyl glycolate, acetyltributyl citrate, dibenzyl sebacate, tricresyl phosphate, and toluene ethylsulfonamide.

Some embodiments of the present compositions can further include a surfactant. Those of ordinary skill will recognize surfactants that can be used with the present compositions and for particular applications. Furthermore, some embodiments of the present compositions can include a solvent. In some embodiments, the solvent includes an alcohol. Exemplary solvents include ethyl alcohol, isopropyl alcohol, and combinations thereof.

The presently-disclosed compositions include an indicator that can visually display a color at least at one pH and/or within a range of pH. The terms "display," "visually display," and the like refer to the characteristic of being visible by the naked eye. The color of the indicator is not particularly limited, and can include purple, blue, green, yellow, orange, red, or combinations thereof. Some indicators can visually display a color at a first pH, which may be within a range of pH, and can be colorless at a second pH, which may be within another range of pH. Thus, the indicators can display a color in a pH-dependent manner. Exemplary indicators include, but are not limited to, those selected from phenolphthalein, thymolphthalein, m-nitrophenol, o-cresolphthalein, and combinations thereof. The indicator can be selected depending on, for example, the color, pH, and sensitivity that is desired in a composition. For instance, in some embodiments, phenolphthalein can visually display a color at about pH 8.0 to about pH 10.0, thymolphthalein can visually display a color at about pH 8.2 to about pH 9.8, m-nitrophenol can visually display a color at about pH 8.8 to about pH 10.5, and o-cresolphthalein can visually display a color at about pH 6.8 to about pH 8.6.

The present compositions can include indicators that are not or that are poorly soluble in water, though it can be beneficial to evenly and widely disperse the indicator throughout a composition to ensure that it displays an even color when applied in an uncured state and/or when a liquid contacts a cured composition. For embodiments that comprise water insoluble or poorly-water soluble indicators, the compositions can be provided with an additional solvent, such as an alcohol selected from isopropyl alcohol, ethyl alcohol, and the like. Additionally or alternatively, indicators can be milled prior to being incorporated into the composition, and in some instances the indicators are milled with water. Milled indicators can form fine dispersions that distribute more evenly and widely through a water-based composition relative to non-milled indicators. This feature advantageously allows the present compositions to effectively incorporate an indicator in a water-based composition, which then allows for a composition to be produced having a lower volatile organic content (VOC) than similar compositions produced by other methods.

Embodiments of the presently-disclosed compositions can have a relatively small amount or no volatile organic compounds, and such compositions can be referred to as low volatile organic compound compositions and zero volatile organic compound compositions, respectively. Zero volatile organic compound compositions can consist of the acrylic wax, water, and the indicator.

Accordingly, the presently-described compositions can comprise an acrylic wax, water, and an indicator. In some embodiments, the composition can include about 5 wt % to about 55 wt % of the acrylic wax, about 40 wt % to about 95 wt % of water, and about 0.01 wt % to about 2.5 wt % of the indicator. Additionally or alternatively, in some embodiments, the composition can include about 35 wt % to about 55 wt % of the acrylic wax, about 40 wt % to about 60 wt % of water, and about 1.0 wt % to about 2.0 wt % of the indicator. As described above, some embodiments can further include an alcohol, and in some instances comprise about 5 wt % to about 55 wt % of the acrylic wax, about 5 wt % to about 25 wt % of an alcohol, about 40 wt % to about 95 wt % of water, and about 0.01 wt % to about 2.5 wt % of the indicator.

In some embodiments, the composition visually displays a color at a first pH, the first pH being higher than a second pH at which the composition is colorless. In this respect, in some embodiments, the composition is further provided with an alkaline material that maintains and/or raises the pH of the composition to a level (e.g., first pH) that permits the composition to visually display a color. Those of ordinary skill will appreciate different alkaline materials that can be provided to adjust the pH of a composition to a desired level. Exemplary alkaline materials include, but are not limited to metal hydroxides, carbonates, bicarbonates, phosphate, and combinations thereof. In certain embodiments of the present compositions, the alkaline material can be selected from sodium hydroxide, sodium carbonate, sodium bicarbonate, potassium carbonate, potassium hydroxide, trisodium phosphate, and combinations thereof. In some embodiments the compositions only comprise sodium carbonate (i.e., soda ash) as an alkaline material.

In some embodiments, the alkaline material, also referred to herein as an "activator," includes a water soluble powder. Without wishing to be bound by theory, in some embodiments, it is believed that liquid water soluble materials, such as amines, evaporate out of the composition as it dries. As such, after the composition is applied to a surface and dried and/or cured, the evaporated liquid water soluble materials will not provide activation of the pH indicator in the dried floor finish. Thus, the liquid water soluble materials will not provide color change when exposed to water. In contrast, the solid powder alkaline materials remains in the composition as it dries. The powder in the dried finish absorbs water that contacts the finish, which increases the pH within the dried finish and "activates" the pH indicator (e.g., causes the finish to change color).

Although different alkaline materials may be used, in some embodiments, sodium carbonate provides increased depth of color and/or duration of color as compared to other materials, such as potassium carbonate or trisodium phosphate. Again, without wishing to be bound by theory, it is believed that the increased depth and/or duration of color provided by sodium carbonate is due to an increased degree of water solubility as compared to other materials. This increased degree of water solubility absorbs a sufficient amount of liquid (e.g., water and/or other liquids with a sufficiently high pH) to penetrate the surface of the finish and retains the absorbed liquid until all liquid from the surface has evaporated and/or been removed. The liquid penetration of the surface finish provides immediate color change and increased color depth, while the retained liquid provides increased duration of color (e.g., until all surface liquid has been removed/evaporated).

In some embodiments, elevated concentrations of the alkaline material may degrade the dried composition, decreasing the stability of the composition and/or forming a streaky floor finish. As such, in some embodiments, the alkaline material is provided in any suitable concentration for facilitating color change without degrading the dried composition. Suitable alkaline material concentrations include, but are not limited to, between about 0.01 wt % to about 3.0 wt %, between about 0.5 wt % to about 2.5 wt %, between about 1.0 wt % to about 2.0 wt %, between about 0.1 wt % to about 5 wt %, or any combination, sub-combination, range, or sub-range thereof. In some embodiments, the alkaline materials are included in an exemplary composition at a concentration of about 0.75 wt % to about 4.0 wt %.

Additionally or alternatively, in some embodiments, the composition includes a pigment dispersant, such as, but not limited to, Disperbyk 190, and/or an anti-foaming agent, such as, but not limited to, anti-foam 1430. Suitable concentrations of the pigment dispersant include, but are not limited to, between about 0.01 wt % and about 2.0 wt %, between about 0.5 wt % and about 2.0 wt %, between about 0.5 wt % and about 1.5 wt %, between about 0.5 wt % and about 1.0 wt %, between about 1.0 wt % and about 1.5 wt %, between about 0 wt % to about 3.0 wt %, or any combination, sub-combination, range, or sub-range thereof In some embodiments, the pigment dispersant is included in an exemplary composition at a concentration of about 0.1 wt % to about 1.5 wt %. Suitable concentrations of the anti-foaming agent include, but are not limited to, between about 0.01 wt % and about 1.0 wt %, between about 0.01 wt % and about 0.5 wt %, between about 0.01 wt % and about 0.1 wt %, between about 0.05 wt % and about 0.1 wt %, between about 0.04 wt % to about 0.5 wt %, or any combination, sub-combination, range, or sub-range thereof. In some embodiments, the anti-foaming agent is included in an exemplary composition at a concentration of about 0.08 wt % to about 0.35 wt %.

The presently-disclosed subject matter further includes methods for making any of the compositions described herein. In some embodiments, a method for making a composition comprises providing an acrylic wax, water, and an indicator, milling the indicator, and mixing the acrylic wax, water, and the milled indicator to form the composition.

In some embodiments, at least water is added to the indicator prior to the milling step, and, optionally, additional water can be added to the composition in the mixing step. In other embodiments, at least the acrylic wax, the water, and the indicator are mixed together prior to the milling step.

Any suitable milling machine known in the art can be utilized. In certain embodiments, the milling step includes milling with a mixer and/or a ceramic media mill. More specifically, in some embodiments, a ceramic media mill performs the milling step, and the ceramic media mill is selected from a pebble mill, a sand mill, and a horizontal mill.

Embodiments of methods for making the present compositions can further comprise adjusting the pH of the composition to a level that permits the indicator to visually display a color. pH adjustment can be accomplished by incorporating an alkaline substance to the composition so that the composition reaches a desired pH (e.g., the first pH). In this manner, the uncured composition will initially visually display a color so that the composition is visible when it is applied to a surface.

Once the composition is applied to a surface, the wet composition can dry into a colorless, cured composition. The term "cured" is used herein to refer to a state in which the liquids in the composition have evaporated, thereby providing a hardened, dry composition. In some instances a cured composition can possess a plastic, flexible, and/or wax-like consistency, and therefore the term cured does not necessarily imply that a composition is hard and inflexible. In some embodiments, a composition can be applied to a surface as a liquid, and the composition can cure at ambient pressure and room temperature to provide a wax-like finish on the surface.

As described herein, as the composition cures it can transition from a color-displaying state to a colorless state. In some instances, a cured composition can return to a color-displaying state upon contacting a liquid, having a sufficiently basic character, such as tap water. This property enables the present compositions to indicate whether surfaces have been coated with a composition when applying the composition. This property also enables the present compositions to indicate whether surfaces are damp or wet, thereby providing a visual notice that a surface is wet even before the wet surface is has been identified.

The presently-disclosed subject matter is further illustrated by the following specific but non-limiting examples.

EXAMPLES

Example 1

This Example describes a method for making and a method for using an embodiment of a composition in accordance with the presently-disclosed subject matter. An acrylic floor wax was provided, and specifically Encor 7076 acrylic floor wax concentrate (i.e., acrylic wax). The Encor 7076 acrylic floor wax concentrate comprised 36 vol % of solids in water. Water, phenolphthalein, and anhydrous sodium carbonate were also provided.

Next, 38.62 pph of the acrylic wax was added to a mixing vessel. After the acrylic wax had been added, 14.13 pph of water was added to the mixing vessel while slowly agitating the mixture. 1.80 pph of the pH indicator were then added, and the entire composition was mixed for about 10 to about 15 minutes.

The mixed composition was then charged into a ceramic ball mill, and the mixture was milled for about 12 to about 15 hours at room temperature. At the end of the milling process, the indicator was evenly dispersed throughout the composition.

The milled composition was then removed from the ceramic ball mill and placed in another mixing vessel. 45.45 pph of a 3% solution of anhydrous sodium carbonate was added to the milled composition, and the milled composition and sodium carbonate were mixed together for about 10 to about 20 minutes at a low speed (i.e., 60 to 120 RPMs).

The resulting composition consisted of 13.90 wt % of acrylic floor wax concentrate solids (i.e., acrylic wax), 82.94 wt % water, 1.80 wt % phenolphthalein, and 1.36 wt % anhydrous sodium carbonate. Accordingly, the composition comprised a total of 17.07 wt % (14.82 vol %) of solids. The composition comprised no volatile organic compounds.

Lastly, the completed composition was filled into one gallon plastic sealable containers for storage. When utilizing the composition, the composition was light pink when it was first applied to a floor surface. As the composition dried and hardened, it transitioned from a light pink color to having no color. However, when water was applied to the cured composition, the cured composition to transition back to a reddish-purple color for as long as the water remained in contact with the dried composition.

Example 2

This Example describes an embodiment of a composition in accordance with the presently-disclosed subject matter that is a "low volatile organic compound" composition. The same procedure as described in Example 1 was followed, and, in addition, triethylamine was added to the mixture prior to the milling step. The amounts of the components were varied so that the final composition comprised the following:

TABLE 1

Low Volatile Organic Compound Composition

| Component | Percent by Weight |
| --- | --- |
| Acrylic Floor Wax Concentrate (solids) | 17.27 |
| Phenolphthalein | 0.22 |
| Water | 81.81 |
| Triethylamine | 0.70 |

Example 3

This Example describes an embodiment of a composition in accordance with the presently-disclosed subject matter that is a "high volatile organic compound" composition. The same procedure as described in Example 1 was followed, and, in addition, triethylamine, isopropyl alcohol, and dimethylethanolamine were added to the mixture prior to the milling step. The amounts of the components were varied so that the final composition comprised the following:

TABLE 2

Low Volatile Organic Compound Composition

| Component | Percent by Weight |
| --- | --- |
| Acrylic Floor Wax Concentrate (solids) | 13.26 |
| Isopropyl Alcohol | 13.09 |
| Phenolphthalein | 0.17 |
| Water | 62.79 |
| Triethylamine | 0.53 |
| Dimethylethanolamine | 10.16 |

Examples 4-15 illustrate test formulations prepared to address the effect of activator type and level on color change, processing variables, product stability, application properties, and changes that may be imparted to produce higher solids and/or lower VOC products. As seen in the examples below, the ability of the composition to change color varies depending on the type of indicator, the other ingredients included in the composition, and/or the method in which the composition is formed. As such, the formation of a composition for indicating the presence of a liquid requires more than addition of a color indicator to a floor wax or optimization of variables.

Example 4

This Example describes an embodiment of a composition in accordance with the presently-disclosed subject matter. The composition was formed by pebble milling, by weight percent of the final composition, 38.615% acrylic wax (i.e., Encor 7074 floor finish concentrate), 1.800% phenolphthalein, and 14.131% tap water for 24-48 hours, then slowly adding a pre-mixed solution including, by weight percent of the final composition, 44.090% tap water and 1.364% sodium carbonate mono-hydrate. The amounts of the components in the final composition comprised the following:

TABLE 3

Composition of Formula No. RA-111-1

| Component | Pounds | Gallons | Percent by Weight |
| --- | --- | --- | --- |
| Encor 7074 Floor Finish Concentrate | 330.40 | 38.196 | 38.615 |
| Phenolphthalein | 15.40 | 1.427 | 1.800 |
| Tap Water | 498.16 | 59.802 | 58.221 |
| Sodium Carbonate Mono-Hydrate | 11.67 | 0.623 | 1.364 |
| Totals | 855.63 | 100.048 | 100.000 |

Typical properties of the composition included:

TABLE 4

Typical Properties of Formula No. RA-111-1

| | |
| --- | --- |
| Weight per Gallon | 8.5563 lbs/gal |
| Activator Level | 9.81% on Acrylic Solids |
| Color | Dark Pink (Fuscia) |
| Total Weight Solids | 17.07% |
| Total Volume Solids | 14.68% |
| VOC | ~2.89% of Total Formula Weight |
| pH | Average of 10.1-10.7 |
| Applied Color | Pink |
| One Coat Dry Time | 30-45 Minutes |
| Visible Color Development | Immediate |
| Depth of Color | Excellent |
| Duration of Color | Retained Until Floor Dried |
| Days Floor Showed Color Changes | <60 |

Example 5

This Example describes an embodiment of a composition in accordance with the presently-disclosed subject matter, the composition having a 50.0% reduction in sodium carbonate as compared to Example 4. The composition was formed by ball milling, by weight percent of the final composition, 10.278% acrylic wax (i.e., Encor 7074 floor finish concentrate), 1.800% phenolphthalein, and 14.131% tap water for 15 hours, adding, by weight percent of the final composition, 28.337% acrylic wax, and then slowly adding a pre-mixed solution including, by weight percent of the final composition, 44.772% tap water and 1.364% sodium carbonate mono-hydrate. The amounts of the components in the final composition comprised the following:

TABLE 5

Composition of Formula No. RA-111-2

| Component | Pounds | Gallons | Percent by Weight |
|---|---|---|---|
| Encor 7074 Floor Finish Concentrate | 409.90 | 47.388 | 38.615 |
| Phenolphthalein | 19.10 | 1.770 | 1.800 |
| Tap Water | 625.26 | 75.061 | 58.903 |
| Sodium Carbonate Mono-Hydrate | 7.24 | 0.386 | 0.682 |
| Totals | 1061.50 | 124.605 | 100.000 |

Typical properties of the composition included:

TABLE 6

Typical Properties of Formula No. RA-111-2

| | |
|---|---|
| Weight per Gallon | 8.528 lbs/gal |
| Activator Level | 4.93% on Acrylic Solids |
| Color | Light Pink |
| Total Weight Solids | 16.38% |
| Total Volume Solids | 14.09% |
| VOC | ~2.90% of Total Formula Weight |
| Applied Color | Very Light Pink |
| One Coat Dry Time | 30-45 Minutes |
| Visible Color Development | 0-15 Seconds |
| Depth of Color | Fair |
| Duration of Color | Retained Until Floor Dried |
| Days Floor Showed Color Changes | <60 |

Example 6

This Example describes an embodiment of a composition in accordance with the presently-disclosed subject matter, the composition having a 33.3% reduction in sodium carbonate as compared to Example 4. The composition was formed by ball milling, by weight percent of the final composition, 10.278% acrylic wax (i.e., Encor 7074 floor finish concentrate), 1.800% phenolphthalein, and 14.131% tap water for 15 hours, adding, by weight percent of the final composition, 28.337% acrylic wax, and then slowly adding a pre-mixed solution including, by weight percent of the final composition, 44.545% tap water and 0.909% sodium carbonate mono-hydrate. The amounts of the components in the final composition comprised the following:

TABLE 7

Composition of Formula No. RA-111-3

| Component | Pounds | Gallons | Percent by Weight |
|---|---|---|---|
| Encor 7074 Floor Finish Concentrate | 409.90 | 47.388 | 38.615 |
| Phenolphthalein | 19.10 | 1.770 | 1.800 |
| Tap Water | 622.85 | 74.771 | 58.676 |
| Sodium Carbonate Mono-Hydrate | 9.65 | 0.515 | 0.909 |
| Totals | 1061.50 | 124.444 | 100.000 |

Typical properties of the composition included:

TABLE 8

Typical Properties of Formula No. RA-111-3

| | |
|---|---|
| Weight per Gallon | 8.530 lbs/gal |
| Activator Level | 6.54% on Acrylic Solids |
| Color | Pink |
| Total Weight Solids | 16.61% |
| Total Volume Solids | 14.21% |
| VOC | ~2.90% of Total Formula Weight |
| pH | 10.42 |
| Applied Color | Light Pink |
| One Coat Dry Time | 30-45 Minutes |
| Visible Color Development | 0-5 Seconds |
| Depth of Color | Good |
| Duration of Color | Retained Until Floor Dried |
| Days Floor Showed Color Changes | <60 |

Example 7

This Example describes an embodiment of a composition including potassium carbonate as an alkaline activator, in accordance with the presently-disclosed subject matter. The composition was formed by ball milling, by weight percent of the final composition, 14.131% distilled water and 1.800% phenolphthalein for 15 hours, adding 38.614% acrylic wax (i.e., Encor 7074 floor finish concentrate), and then slowly adding a pre-mixed solution including, by weight percent of the final composition, 44.091% distilled water and 1.364% potassium carbonate. The amounts of the components in the final composition comprised the following:

TABLE 9

Composition of Formula No. RA-140-1

| Component | Pounds | Gallons | Percent by Weight |
|---|---|---|---|
| Distilled Water | 618.03 | 74.192 | 58.222 |
| Phenolphthalein | 19.10 | 1.770 | 1.800 |
| Encor 7074 Floor Finish Concentrate | 409.90 | 47.388 | 38.614 |
| Potassium Carbonate | 14.48 | 0.715 | 1.364 |
| Totals | 1061.50 | 124.065 | 100.000 |

Typical properties of the composition included:

TABLE 10

Typical Properties of Formula No. RA-140-1

| | |
|---|---|
| Weight per Gallon | 8.556 lbs/gal |
| Activator Level | 9.81% on Acrylic Solids |
| Color | Dark Pink |
| Total Weight Solids | 17.07% |
| Total Volume Solids | 14.42% |
| VOC | ~2.90% of Total Formula Weight |
| pH | 10.74 |
| Applied Color | Light Pink |
| One Coat Dry Time | 30-45 Minutes |
| Visible Color Development | 30-40 Seconds |
| Depth of Color | Fair |
| Duration of Color | Retained Until Floor Dried |
| Days Floor Showed Color Changes | >10 |

Example 8

This Example describes an embodiment of a composition including trisodium phosphate dodecahydrate as an alkaline activator, in accordance with the presently-disclosed subject matter. The composition was formed by ball milling, by weight percent of the final composition, 14.131% distilled water and 1.800% phenolphthalein for 15 hours, adding 38.614% acrylic wax (i.e., Encor 7074 floor finish concentrate), and then slowly adding a pre-mixed solution including, by weight percent of the final composition, 44.091% distilled water and 1.364% trisodium phosphate dodecahydrate. The amounts of the components in the final composition comprised the following:

TABLE 11

Composition of Formula No. RA-141-1

| Component | Pounds | Gallons | Percent by Weight |
|---|---|---|---|
| Distilled Water | 618.03 | 74.192 | 58.222 |
| Phenolphthalein | 19.10 | 1.770 | 1.800 |
| Encor 7074 Floor Finish Concentrate | 409.90 | 47.388 | 38.614 |
| Potassium Carbonate | 14.48 | 1.051 | 1.364 |
| Totals | 1061.50 | 124.401 | 100.000 |

Typical properties of the composition included:

TABLE 12

Typical Properties of Formula No. RA-141-1

| Weight per Gallon | 8.556 lbs/gal |
|---|---|
| Activator Level | 9.81% on Acrylic Solids |
| Color | Dark Pink |
| Total Weight Solids | 17.07% |
| Total Volume Solids | 14.65% |
| VOC | ~2.90% of Total Formula Weight |
| pH | 10.20 |
| Applied Color | Light Pink |
| One Coat Dry Time | 30-45 Minutes |
| Visible Color Development | 40-60 Seconds |
| Depth of Color | Poor/Very Light Pink |
| Duration of Color | Retained Until Floor Dried |
| Days Floor Showed Color Changes | >15 |

Example 9

This Example describes an embodiment of a composition in accordance with the presently-disclosed subject matter, the composition having a 50.0% reduction in sodium carbonate as compared to Example 4 along with addition of low level potassium hydroxide (KOH). The composition was formed by ball milling, by weight percent of the final composition, 14.074% distilled water and 1.792% phenolphthalein for 15 hours, slowly adding 38.461% acrylic wax (i.e., Encor 7074 floor finish concentrate), slowly adding a pre-mixed solution including, by weight percent of the final composition, 44.594% distilled water and 0.679% sodium carbonate mono-hydrate, and then, after mixing well, adding, by weight percent of the final composition, .45% potassium hydroxide (KOH). The amounts of the components in the final composition comprised the following:

TABLE 13

Composition of Formula No. RA-142-1

| Component | Pounds | Gallons | Percent by Weight |
|---|---|---|---|
| Encor 7074 Floor Finish Concentrate | 409.90 | 47.388 | 38.461 |
| Phenolphthalein | 19.10 | 1.770 | 1.792 |

TABLE 13-continued

Composition of Formula No. RA-142-1

| Component | Pounds | Gallons | Percent by Weight |
|---|---|---|---|
| Distilled Water | 625.26 | 75.061 | 58.668 |
| Sodium Carbonate Mono-Hydrate | 7.24 | 0.386 | 0.679 |
| Potassium Hydroxide (KOH) | 4.26 | 0.390 | 0.400 |
| Totals | 1065.76 | 124.995 | 100.000 |

Typical properties of the composition included:

TABLE 14

Typical Properties of Formula No. RA-142-1

| Weight per Gallon | 8.526 lbs/gal |
|---|---|
| Activator Level | 4.91% Sodium Carbonate Mono-Hydrate |
| | 1.30% Potassium Hydroxide |
| Total Weight Solids | 16.50% |
| Total Volume Solids | 14.14% |
| VOC | ~2.89% of Total Formula Weight |
| pH | 10.22 |
| Applied Color | Very Light Pink |
| One Coat Dry Time | 30-45 Minutes |
| Visible Color Development | 5-15 Seconds |
| Depth of Color | Fair |
| Duration of Color | Retained Until Floor Dried |
| Days Floor Showed Color Changes | >10 |

Example 10

This Example describes an embodiment of a composition in accordance with the presently-disclosed subject matter. The composition includes the same components and concentrations as Example 4, however, the order of component addition was changed. More specifically, the composition was formed by ball milling, by weight percent of the final composition, 14.131% distilled water and 1.800% phenolphthalein for 24 hours, slowly adding a pre-mixed solution including, by weight percent of the final composition, 44.090% distilled water and 1.364% sodium carbonate mono-hydrate, and then, after mixing well, adding, by weight percent of the final composition, 38.615% acrylic wax (i.e., Encor 7074 floor finish concentrate). The amounts of the components in the final composition comprised the following:

TABLE 15

Composition of Formula No. RA-138-1

| Component | Pounds | Gallons | Percent by Weight |
|---|---|---|---|
| Encor 7074 Floor Finish Concentrate | 409.90 | 47.387 | 38.615 |
| Phenolphthalein | 19.10 | 1.770 | 1.800 |
| Distilled Water | 618.02 | 74.192 | 58.221 |
| Sodium Carbonate Mono-Hydrate | 14.48 | 0.773 | 1.364 |
| Totals | 1061.50 | 124.122 | 100.000 |

Typical properties of the composition included:

TABLE 16

Typical Properties of Formula No. RA-138-1

| Weight per Gallon | 8.552 lbs/gal |

TABLE 16-continued

Typical Properties of Formula No. RA-138-1

| | |
|---|---|
| Activator Level | 9.81% |
| Total Weight Solids | 17.07% |
| Total Volume Solids | 14.46% |
| VOC | ~2.90% of Total Formula Weight |
| pH | 10.45 |
| Applied Color | Pink |
| One Coat Dry Time | 30-45 Minutes |
| Visible Color Development | Immediate |
| Depth of Color | Excellent |
| Duration of Color | Retained Until Floor Dried |
| Days Floor Showed Color Changes | <30 |

Example 11

This Example describes an embodiment of a low odor, low VOC composition in accordance with the presently-disclosed subject matter. The composition was formed by ball milling, by weight percent of the final composition, 10.195% acrylic wax (i.e., Encor 7070 floor finish concentrate), 1.785% phenolphthalein, and 14.017% tap water for 20 hours, adding, by weight percent of the final composition, 28.109% acrylic wax, and then slowly adding a pre-mixed solution including, by weight percent of the final composition, 43.734% tap water and 2.160% sodium carbonate. The amounts of the components in the final composition comprised the following:

TABLE 17

Composition of Formula No. RA-114-2

| Component | Pounds | Gallons | Percent by Weight |
|---|---|---|---|
| Encor 7074 Floor Finish Concentrate | 409.90 | 47.332 | 38.304 |
| Phenolphthalein | 19.10 | 1.770 | 1.785 |
| Tap Water | 618.02 | 74.192 | 57.751 |
| Sodium Carbonate Mono-Hydrate | 23.11 | 1.140 | 2.160 |
| Totals | 1070.13 | 124.435 | 100.000 |

Typical properties of the composition included:

TABLE 18

Typical Properties of Formula No. RA-114-2

| | |
|---|---|
| Weight per Gallon | 8.600 lbs/gal |
| Activator Level | 15.66% on Acrylic Solids |
| Total Weight Solids | 17.73% |
| VOC | ~2.87% of Total Formula Weight |
| pH | 10.00 |
| Applied Color | Pink |
| One Coat Dry Time | 30-45 Minutes |
| Visible Color Development | Poor Initially - Improved With Aging |
| Depth of Color | Poor Initially - Improved With Aging |
| Duration of Color | Retained Until Floor Dried |
| Days Floor Showed Color Changes | <60 |

Example 12

This Example describes an embodiment of a composition in accordance with the presently-disclosed subject matter, the composition being similar to that of Example 4 with the addition of a pigment dispersant and an anti-foam agent. The composition was formed by pebble milling, by weight percent of the final composition, 13.993% distilled water, 0.886% disperbyk 190, 0.093% anti-foam 1430, and 1.782% phenolphthalein for 12-15 hours, slowly adding, by weight percent of the final composition, 38.237% acrylic wax (i.e., Encor 7074 floor finish concentrate), and then slowly adding a pre-mixed solution including, by weight percent of the final composition, 43.657% distilled water and 1.352% sodium carbonate mono-hydrate. The amounts of the components in the final composition comprised the following:

TABLE 19

Composition of Formula No. RA-154-1

| Component | Pounds | Gallons | Percent by Weight |
|---|---|---|---|
| Encor 7074 Floor Finish Concentrate | 409.90 | 47.39 | 38.237 |
| Phenolphthalein | 19.1 | 1.77 | 1.782 |
| Distilled Water | 618.0 | 74.20 | 57.65 |
| Sodium Carbonate Mono-Hydrate | 14.5 | 0.77 | 1.352 |
| Disperbyk 190 | 9.5 | 1.08 | 0.886 |
| Anti-Foam 1430 | 1.0 | 0.12 | 0.093 |
| Totals | 1072.0 | 125.33 | 100.000 |

Typical properties of the composition included:

TABLE 20

Typical Properties of Formula No. RA-154-1

| | |
|---|---|
| Weight per Gallon | 8.553 lbs/gal |
| Activator Level | 9.83% on Acrylic Solids |
| Total Weight Solids | 17.35% |
| Total Volume Solids | 15.10% |
| VOC | ~2.87% of Total Formula Weight |
| pH | 10.69 |
| Applied Color | Pink |
| One Coat Dry Time | 30-45 Minutes |
| Visible Color Development | Immediate |
| Depth of Color | Excellent |
| Duration of Color | Retained Until Floor Dried |
| Days Floor Showed Color Changes | <45 |

Example 13

This Example describes an embodiment of a composition in accordance with the presently-disclosed subject matter, the composition including a higher concentration of solids as compared to that of Example 12. The composition was formed by pebble milling, by weight percent of the final composition, 13.901% distilled water, 0.882% disperbyk 190, 0.093% anti-foam 1430, and 1.764% phenolphthalein for 12-15 hours, slowly adding, by weight percent of the final composition, 51.044% acrylic wax (i.e., Encor 7074 floor finish concentrate), and then slowly adding a pre-mixed solution including, by weight percent of the final composition, 30.506% distilled water and 1.810% sodium carbonate mono-hydrate. The amounts of the components in the final composition comprised the following:

TABLE 21

Composition of Formula No. RA-160-1

| Component | Pounds | Gallons | Percent by Weight |
|---|---|---|---|
| Encor 7074 Floor Finish Concentrate | 439.9 | 50.86 | 51.044 |
| Phenolphthalein | 15.2 | 1.41 | 1.764 |
| Distilled Water | 382.7 | 45.94 | 44.407 |
| Sodium Carbonate Mono-Hydrate | 15.6 | 0.83 | 1.810 |

TABLE 21-continued

Composition of Formula No. RA-160-1

| Component | Pounds | Gallons | Percent by Weight |
|---|---|---|---|
| Disperbyk 190 | 7.6 | 0.86 | 0.882 |
| Anti-Foam 1430 | 0.8 | 0.10 | 0.093 |
| Totals | 861.8 | 100.00 | 100.000 |

Typical properties of the composition included:

TABLE 22

Typical Properties of Formula No. RA-160-1

| | |
|---|---|
| Weight per Gallon | 8.618 lbs/gal |
| Activator Level | 9.85% on Acrylic Solids |
| Total Weight Solids | 22.40% |
| Total Volume Solids | 19.68% |
| VOC | ~3.83% of Total Formula Weight |
| pH | 10.55 |
| Applied Color | Pink |
| One Coat Dry Time | 30-45 Minutes |
| Visible Color Development | Immediate |
| Depth of Color | Excellent |
| Duration of Color | Retained Until Floor Dried |
| Days Floor Showed Color Changes | <60 |

Example 14

This Example describes an embodiment of a composition in accordance with the presently-disclosed subject matter, the composition including a higher concentration of solids as compared to that of Example 12. The composition was formed by pebble milling, by weight percent of the final composition, 13.951% distilled water, 0.885% disperbyk 190, 0.093% anti-foam 1430, and 1.770% phenolphthalein for 12-15 hours, slowly adding, by weight percent of the final composition, 44.906% acrylic wax (i.e., Encor 7074 floor finish concentrate), and then slowly adding a pre-mixed solution including, by weight percent of the final composition, 36.800% distilled water and 1.595% sodium carbonate mono-hydrate. The amounts of the components in the final composition comprised the following:

TABLE 23

Composition of Formula No. RA-161-1

| Component | Pounds | Gallons | Percent by Weight |
|---|---|---|---|
| Encor 7074 Floor Finish Concentrate | 385.6 | 44.58 | 44.906 |
| Phenolphthalein | 15.2 | 1.41 | 1.770 |
| Distilled Water | 435.8 | 52.32 | 50.751 |
| Sodium Carbonate Mono-Hydrate | 13.7 | 0.73 | 1.595 |
| Disperbyk 190 | 7.6 | 0.86 | 0.885 |
| Anti-Foam 1430 | 0.8 | 0.10 | 0.093 |
| Totals | 858.7 | 100.00 | 100.000 |

Typical properties of the composition included:

TABLE 24

Typical Properties of Formula No. RA-161-1

| | |
|---|---|
| Weight per Gallon | 8.587 lbs/gal |
| Activator Level | 9.87% on Acrylic Solids |
| Total Weight Solids | 19.97% |
| Total Volume Solids | 17.47% |
| VOC | ~3.37% of Total Formula Weight |
| pH | 10.65 |
| Applied Color | Pink |
| One Coat Dry Time | 30-45 Minutes |
| Visible Color Development | Immediate |
| Depth of Color | Excellent |
| Days Floor Showed Color Changes | <60 |

Example 15

This Example describes an embodiment of a composition in accordance with the presently-disclosed subject matter, the composition including a higher pH as compared to that of Example 14. The composition was formed by pebble milling, by weight percent of the final composition, 13.435% distilled water, 0.852% disperbyk 190, 0.090% anti-foam 1430, and 1.705% phenolphthalein for 12-15 hours, slowly adding, by weight percent of the final composition, 43.243% acrylic wax (i.e., Encor 7074 floor finish concentrate), and then slowly adding a pre-mixed solution including, by weight percent of the final composition, 38.982% distilled water and 1.693% sodium carbonate mono-hydrate. The amounts of the components in the final composition comprised the following:

TABLE 25

Composition of Formula No. RA-161-2

| Component | Pounds | Gallons | Percent by Weight |
|---|---|---|---|
| Encor 7074 Floor Finish Concentrate | 385.6 | 44.58 | 43.243 |
| Phenolphthalein | 15.2 | 1.41 | 1.705 |
| Distilled Water | 467.4 | 56.11 | 52.417 |
| Sodium Carbonate Mono-Hydrate | 15.1 | 0.81 | 1.693 |
| Disperbyk 190 | 7.6 | 0.86 | 0.852 |
| Anti-Foam 1430 | 0.8 | 0.10 | 0.090 |
| Totals | 891.7 | 103.87 | 100.000 |

Typical properties of the composition included:

TABLE 26

Typical Properties of Formula No. RA-161-2

| | |
|---|---|
| Weight per Gallon | 8.585 lbs/gal |
| Activator Level | 10.88% on Acrylic Solids |
| Total Weight Solids | 19.39% |
| Total Volume Solids | 16.89`% |
| VOC | ~3.24% of Total Formula Weight |
| pH | 10.85 |
| Applied Color | Pink |
| One Coat Dry Time | 30-45 Minutes |
| Visible Color Development | Immediate |
| Depth of Color | Excellent |
| Duration of Color | Retained Until Floor Dried |
| Days Floor Showed Color Changes | <70 |

As will be understood by those of ordinary skill in the art, some of the Examples described above are more advantageous than others. For instance, Example 15 (RA-161-2), which includes sodium carbonate mono-hydrate, a pigment dispersant, and an anti-foam agent, has a lower VOC content than Examples 13 and 14, provides immediate visible color development with excellent color of depth, and shows color changes for up to 70 days or more. More specifically, it was observed that Example 15 provided a more rapid color change, developed a deeper color, and retained the ability to change color for a longer period of time relative to Examples 13 and 14.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A floor coating composition, comprising:
    acrylic wax in an amount of about 10 wt % to about 55 wt % of the total composition;
    water in an amount of about 40 wt % to about 95 wt % of the total composition;
    phenolphthalein in an amount of about 0.01 wt % to about 2.5 wt % of the total composition; and
    sodium carbonate mono-hydrate in an amount of about 0.01 wt % to about 3.0 wt % of the total composition.

2. The composition of claim 1, wherein the acrylic wax further includes styrene.

3. The composition of claim 1, further comprising an additional solvent.

4. The composition of claim 3, wherein the additional solvent includes ethanol, isopropyl alcohol, or a combination thereof.

5. The composition of claim 1, further comprising:
    a pigment dispersant in an amount of about 0.01 wt % to about 2.0 wt % of the total composition; and
    an anti-foaming agent in an amount of about 0.01 wt % to about 1.0 wt % of the total composition.

* * * * *